May 15, 1973
D. K. DILLON ET AL
Plant Pat. 3,337
CHRYSANTHEMUM PLANT
Filed Sept. 14, 1971
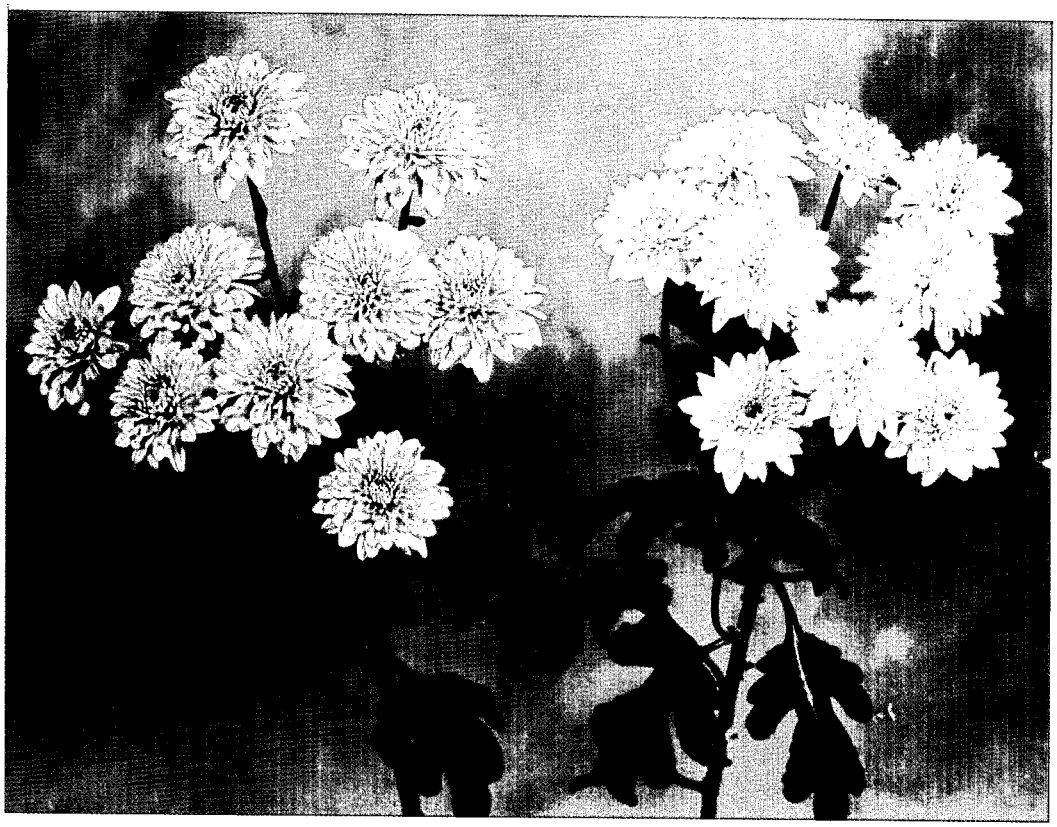

United States Patent Office

Plant Pat. 3,337
Patented May 15, 1973

3,337
CHRYSANTHEMUM PLANT

Douglas K. Dillon, Bloomsburg, Pa., and Walter H. Jessel, Jr., Doylestown, and William E. Duffett, Akron, Ohio, assignors to Douglas K. Dillon, Bloomsburg, Pa.

Filed Sept. 14, 1971, Ser. No. 180,530
Int. Cl. A01h *5/00*
U.S. Cl. Plt.—79 1 Claim The present invention comprises a new and distinct cultivar of chrysanthemum plant which is a sport of the unpatented cultivar known in the United States as Show-Off.

The new cultivar is similar in many respects to Show-Off, having the same characteristics of:

(1) Plant habit.
(2) Flower size and form.
(3) Flowering response.

The new cultivar is distinguished from Show-Off by its red-bronze flower color.

The new cultivar was discovered at Bloomsburg, Pa., and when subsequently asexually reproduced by cuttings at Barberton, Ohio, has been found to retain its distinctive characteristics through successive propagations.

The new cultivar when grown in the vicinity of Barberton, Ohio, has a response period of approximately 9 weeks, and the following detailed description is based on observations made of the new cultivar in a greenhouse in Barberton, Ohio. The response time, blooming period, color, and total vigor may vary significantly with varying environmental conditions such as temperature, day length, and light intensity. Suggested flowering in the northern and western United States is from mid-April through October; coastal California, mid-March through October; Florida, mid-December through April.

The accompanying photographic drawing shows the unique characteristics of the new cultivar, the color being as nearly true as possible with color illustrations of this type. In the drawing, the new cultivar appears on the left and the parent cultivar Show-Off on the right. In the description which follows, color references are to the Munsell Color Book, 1963 edition, and color comparisons are made with the cultivar Show-Off.

Botanical classification: *Chrysanthemum morifolium.*

Bloom:

*Size.*—2½".
*Fully expanded.*—3⅛".
*Borne.*—Clusters on elongated pedicels.
*Stems.*—Strong.
*Form.*—Decorative.
*Permanence.*—10–12 days.

| Color | Red Show-Off | Show-Off |
|---|---|---|
| Center of flower | Orange bronze, 1.25YR5/12. | Gold yellow, 1.25Y7/12. |
| Base of petals | Yellow, 7.5Y8.5/8 | Yellow, 7.5Y8.5/8. |
| Inside of petals | Red bronze, 10R4/12 to orange bronze, 1.25YR5/12. | Gold bronze, 10YR7/10 to gold yellow, 2.5Y8/10. |
| Reverse of petals | Light bronze, 7.5YR7/6 to yellow bronze, 7.5Y8.5/8. | Light yellow, 7.5Y9/6. |
| Tonality from a distance. | Red bronze | Gold bronze. |
| Discoloration | Red bronze, 1.25YR5/12. | Gold yellow, 2.5Y8/10. |

Petals:

*Texture.*—Smooth.
*Appearance and form.*—Open at base, broadening quickly to wide flat keel, tapering to a blunt point.
*Arrangement.*—Composite, whorled on a single receptacle.
*Persistence.*—Resist shatter.
*Fragrance.*—Typical chrysanthemum.

Reproductive organs:

*Stamen, anthers.*—0 to 15.
*Pollen.*—None to scant.
*Arrangement.*—Clustered in center of flower, if present.
*Styles.*—Present both ray and disc florets.
*Length.*—Short.
*Ovaries.*—At the base of petal attached to receptacle.

Plant:

*Form.*—Herbaceous.
*Growth.*—Upright.
*Height.*—Approximately 40" when grown as a single stem crop with 2–3 long day weeks and 11–12 weeks total crop time during the various seasons of the year as defined in the timetables published by Yoder Brothers, Inc.
*Spread.*—None when grown single stem to slight when pinched.

Foliage:

*Top side.*—Dark Green, 7.5GY3/4.
*Size.*—5½"–6½" long, 3½" wide.
*Quantity.*—Numerous.
*Shape.*—Spatulate lobed.
*Texture.*—Smooth.
*Ribs and veins.*—Prominent.
*Edge.*—Deeply indented.
*Serration.*—Moderate.
*Under side.*—Light green, 7.5GY5/4.
*Stipules.*—Rudimentary.

We claim:

1. A new and distinct cultivar of chrysanthemum characterized particularly as to its uniqueness when compared to the parent cultivar Show-Off by its red-bronze flower color.

No references cited.

ROBERT E. BAGWILL, Primary Examiner